United States Patent
Ye

(10) Patent No.: US 10,961,192 B2
(45) Date of Patent: Mar. 30, 2021

(54) (R)-4-HYDROXY-2-OXO-1-PYRROLIDINE-ACETAMIDE CRYSTAL FORM, PREPARATION METHOD THEREFOR, AND APPLICATION THEREOF

(71) Applicant: CHONGQING RUZER PHARMACEUTICAL COMPANY LIMITED, Chongqing (CN)

(72) Inventor: Lei Ye, Chongqing (CN)

(73) Assignee: CHONGQING RUZER PHARMACEUTICAL COMPANY LIMITED, Chongqing (CN)

(*) Notice: Subject to any disclaimer, the term of this patent is extended or adjusted under 35 U.S.C. 154(b) by 10 days.

(21) Appl. No.: 16/476,477

(22) PCT Filed: Dec. 25, 2017

(86) PCT No.: PCT/CN2017/118180
§ 371 (c)(1),
(2) Date: Jul. 8, 2019

(87) PCT Pub. No.: WO2018/130063
PCT Pub. Date: Jul. 19, 2018

(65) Prior Publication Data
US 2019/0367454 A1    Dec. 5, 2019

(30) Foreign Application Priority Data

Jan. 12, 2017   (CN) .......................... 201710021990.0

(51) Int. Cl.
C07D 207/46    (2006.01)
A61K 9/20      (2006.01)
A61K 9/48      (2006.01)

(52) U.S. Cl.
CPC .......... *C07D 207/46* (2013.01); *A61K 9/2095* (2013.01); *A61K 9/4858* (2013.01); *C07B 2200/13* (2013.01)

(58) Field of Classification Search
CPC .................................................. C07D 207/46
See application file for complete search history.

(56) References Cited

U.S. PATENT DOCUMENTS

| 4,124,594 A | 11/1978 | Monguzzi |
| 4,173,569 A | 11/1979 | Banfi |
| 10,556,863 B1 * | 2/2020 | Ye ...................... C07D 207/273 |
| 2019/0256464 A1 | 8/2019 | Ye |

FOREIGN PATENT DOCUMENTS

| CN | 102249977 A | 11/2011 |
| CN | 102442936 A | 5/2012 |
| CN | 102600130 A | 7/2012 |
| CN | 102603607 A | 7/2012 |
| CN | 103553998 A | 2/2014 |
| CN | 105330582 A | 2/2016 |
| CN | 105820101 A | 8/2016 |
| CN | 106166150 A | 11/2016 |
| KR | 20060010000 | 2/2006 |
| WO | 2018076782 | 5/2018 |
| WO | 2018076783 | 5/2018 |
| WO | 2018076784 | 5/2018 |
| WO | 2018130063 | 7/2018 |

OTHER PUBLICATIONS

Almeida, J. et al., "New Enantioselective Synthesis of 4-Hydroxy-2-Oxypyrrolidine-N-Acetamide (Oxiracetam) from Malic Acid", Tethrahedron: Asymmetry, 3(11):1431-40, (1992).
Chen, X. et al., "Synthesis of (R) 4-Hydroxy-Oxo-1-Pyrrolidineacetamide", Fine Chemical Intermediates, 41(5):21-3, (2011).
International Application No. PCT/CN2017/092219; International Search Report (with translation) and Written Opinion of the International Searching Authority, dated Oct. 11, 2017; 9 pages.
International Application No. PCT/CN2017/092220; International Search Report (with translation) and Written Opinion of the International Searching Authority, dated Oct. 11, 2017; 8 pages.
International Application No. PCT/CN2017/092221; International Search Report (with translation) and Written Opinion of the International Searching Authority, dated Sep. 27, 2017; 16 pages.
International Application No. PCT/CN2017/118180; International Search Report (with translation) and Written Opinion of the International Searching Authority, dated Apr. 4, 2018; 12 pages.
Miyamoto, S., "Synthesis of 4-Hydroxy-2-Pyrrolidinone Derivatives", Neurosciences, 11:1-8, (1985).

* cited by examiner

*Primary Examiner* — Matthew P Coughlin
(74) *Attorney, Agent, or Firm* — Dennis A. Bennett; John Desper

(57) ABSTRACT

The present invention provides an (R)-4-hydroxy-2-oxo-1-pyrrolidineacetamide crystal form, which has diffraction peaks when 2θ is 12.423±0.2°, 16.465±0.2°, 17.344±0.2°, 21.889±0.2°, and 25.054±0.2°. The present invention can promote synthesis of phosphorylcholine and phosphoethanolamine and promote cerebral metabolism, has a stimulating effect on the specific central nervous pathway through the blood-brain barrier, and has special biological activity in the fields of sedation, anti-epilepsy, etc. The (R)-4-hydroxy-2-oxo-1-pyrrolidineacetamide crystal form in the present invention has a melting point peak temperature of 133.1±2° C. and a solubility in water of greater than or equal to 100 mg/mL, dissolves fast in water, provides high bioavailability, good stability, and good particle fluidity, is suitable for production of pharmaceutical preparations and storage and transportation. The crystal form is suitable for preparation into a variety of pharmaceutical compositions, and can be prepared into a variety of preparations, such as tablets, capsules, dripping pills, sustained-release controlled-release preparations, lyophilized powder injections, etc. The preparation method of the present invention is simple and suitable for industrial production.

14 Claims, 4 Drawing Sheets

(R)-4-HYDROXY-2-OXO-1-PYRROLIDINE-ACETAMIDE CRYSTAL FORM, PREPARATION METHOD THEREFOR, AND APPLICATION THEREOF

CROSS-REFERENCE TO RELATED APPLICATION

This application is a national stage entry of PCT/CN2017/118180, filed Dec. 25, 2017, which claims priority to Chinese patent application no. 201710021990.0, filed Jan. 12, 2017, the disclosures of which are hereby incorporated by reference as if written herein in their entireties.

TECHNICAL FIELD

The present invention relates to (R)-4-hydroxy-2-oxo-1-pyrrolidineacetamide, in particular to a crystalline form of (R)-4-hydroxy-2-oxo-1-pyrrolidineacetamide, and a preparation method and use thereof.

BACKGROUND ART (R)-4-hydroxy-2-oxo-1-pyrrolidineacetamide (CAS No. 68252-28-8), which is the dextroisomer of the nootropic drug 4-hydroxy-2-oxo-1-pyrrolidoneacetamide. The latest research shows that the compound has special biological activity in the fields of sedation, anti-epileptic, etc., and has low toxicity and a broad range of pharmaceutical safety, which is expected to become an alternative to the existing highly toxic anti-epileptic drugs. The specific structure of (R)-4-hydroxy-2-oxo-1-pyrrolidineacetamide is as follows:

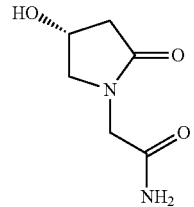

(R)-4-hydroxy-2-oxo-1-pyrrolidineacetamide

In order to effectively develop (R)-4-hydroxy-2-oxo-1-pyrrolidone acetamide into a pharmaceutical product, a solid form with easy to manufacture and acceptable chemical and physical stability is required to facilitate its processing and circulating storage. The crystalline solid form is generally superior to the amorphous form in terms of enhancing the purity and stability of the compound. At present, there are few studies preparation methods and crystalline forms of (R)-4-hydroxy-2-oxo-1-pyrrolidineacetamide, and no crystalline form of (R)-4-hydroxy-2-oxo-1-pyrrolidinoacetamide has been disclosed.

SUMMARY OF THE INVENTION

In order to solve the problems in the prior art, according to a first aspect of the present invention, an object of the present invention is to provide a crystalline form of (R)-4-hydroxy-2-oxo-1-pyrrolidineacetamide. The complete characteristics of the present invention are described below, but for convenience, the provided crystalline form of (R)-4-hydroxy-2-oxo-1-pyrrolidineacetamide provided is referred to as "crystalline form I of (R)-4-hydroxy-2-oxo-1-pyrrolidine acetamide".

Unless otherwise indicated, the parts stated in the present invention are all parts by weight, and the percentages are all percentages by mass.

The object of the invention is achieved by:

A crystalline form I of (R)-4-hydroxy-2-oxo-1-pyrrolidineacetamide having diffraction peaks at diffraction angles 2θ of 12.423±0.2°, 16.465±0.2°, 17.344±0.2°, 21.889±0.2°, and 25.054±0.2°.

The relative peak intensity of the crystalline form I of (R)-4-hydroxy-2-oxo-1-pyrrolidineacetamide of the present invention at a diffraction angle 2θ of 17.344±0.2° is 100%; the relative peak intensity at the diffraction angle 2θ of 16.465±0.2° is greater than 90% and less than 100%, the relative peak intensities at the diffraction angles 2θ of 12.423±0.2°, 21.889±0.2°, and 25.054±0.2° are not less than 70%.

Further, the crystalline form I of (R)-4-hydroxy-2-oxo-1-pyrrolidineacetamide of the present invention has diffraction peaks at diffraction angles 2θ of 12.423±0.2°, 16.285±0.2°, 16.465±0.2°, 17.344±0.2°, 20.707±0.2°, 21.889±0.2°, 25.054±0.2°, and 35.138±0.2°.

Furthermore, the crystalline form I of (R)-4-hydroxy-2-oxo-1-pyrrolidineacetamide of the present invention has diffraction peaks at diffraction angles 2θ of 12.423±0.2°, 14.928±0.2°, 16.285±0.2°, 16.465±0.2°, 17.344±0.2°, 19.198±0.2°, 20.459±0.2°, 20.707±0.2°, 21.548±0.2°, 21.889±0.2°, 23.203±0.2°, 25.054±0.2°, 26.117±0.2°, 29.913±0.2°, 30.49±0.2°, 35.138±0.2°, 37.569±0.2°, and 37.972±0.2°. Specifically, the crystalline form I of (R)-4-hydroxy-2-oxo-1-pyrrolidineacetamide of the present invention has a powder diffraction pattern as shown in FIG. 1.

The crystalline form I of (R)-4-hydroxy-2-oxo-1-pyrrolidineacetamide of the present invention has the following—X-ray powder diffraction data expressed by d(Å) value and relative intensity percentage I (%) value,

| d (Å) | I (%) |
| --- | --- |
| 7.1193 | 73 |
| 5.9296 | 15.6 |
| 5.4386 | 46.2 |
| 5.3794 | 95.1 |
| 5.1086 | 100 |
| 4.6193 | 22.6 |
| 4.3374 | 28.4 |
| 4.286 | 43.5 |
| 4.1205 | 12.9 |
| 4.0572 | 83.1 |
| 3.8303 | 14.5 |
| 3.5513 | 73.1 |
| 3.4092 | 19.1 |
| 2.9846 | 36.7 |
| 2.9295 | 35.4 |
| 2.5519 | 44.8 |
| 2.3921 | 15 |
| 2.3677 | 18.4 |

The unit cell of the crystalline form I of (R)-4-hydroxy-2-oxo-1-pyrrolidineacetamide of the present invention is Orthorhombic (orthogonal crystal system), a=14.12 Å, b=5.82 Å, and c=8.704 Å. Specifically, the crystalline form I of (R)-4-hydroxy-2-oxo-1-pyrrolidineacetamide of the present invention has a crystalline structure diagrams described in FIG. 2.

The peak temperature of the melting point of the crystalline form I of (R)-4-hydroxy-2-oxo-1-pyrrolidineacetamide of the present invention is 133.1±2° C. Specifically, the crystalline form I of (R)-4-hydroxy-2-oxo-1-pyrrolidineacetamide of the present invention has a differential scanning calorimetry (DSC) pattern as shown in FIG. 3.

Further, the crystalline form I of (R)-4-hydroxy-2-oxo-1-pyrrolidineacetamide of the present invention has diffraction peaks at diffraction angles 2θ of 12.423±0.2°, 14.928±0.2°, 16.285±0.2°, 16.465±0.2°, 17.344±0.2°, 19.198±0.2°, 20.459±0.2°, 20.707±0.2°, 21.548±0.2°, 21.889±0.2°, 23.203±0.2°, 25.054±0.2°, 26.117±0.2°, 29.913±0.2°, 30.49±0.2°, 35.138±0.2°, 37.569±0.2°, and 37.972±0.2°; The endothermic transition temperature is 133.1±2° C.

The infrared spectrum generated by crystalline form I of (R)-4-hydroxy-2-oxo-1-pyrrolidineacetamide of the present invention shows absorption peaks at the following wave numbers:

3413 ($cm^{-1}$), 3353 ($cm^{-1}$), 3182 ($cm^{-1}$), 2961 ($cm^{-1}$), 2880 ($cm^{-1}$), 2797 ($cm^{-1}$), 1671 ($cm^{-1}$), 1491 ($cm^{-1}$), 1452 ($cm^{-1}$), 1398 ($cm^{-1}$), 1308 ($cm^{-1}$), 1240 ($cm^{-1}$), 1199 ($cm^{-1}$), 1081 ($cm^{-1}$), 1037 ($cm^{-1}$), 1012 ($cm^{-1}$), 947 ($cm^{-1}$), 671 ($cm^{-1}$), 613 ($cm^{-1}$), 462 ($cm^{-1}$). Specifically, the crystalline form I of (R)-4-hydroxy-2-oxo-1-pyrrolidineacetamide of the present invention has an infrared spectrum as shown in FIG. 4.

Further, the crystalline form I of (R)-4-hydroxy-2-oxo-1-pyrrolidineacetamide of the present invention has diffraction peaks at diffraction angles 2θ of 12.423±0.2°, 14.928±0.2°, 16.285±0.2°, 16.465±0.2°, 17.344±0.2°, 19.198±0.2°, 20.459±0.2°, 20.707±0.2°, 21.548±0.2°, 21.889±0.2°, 23.203±0.2°, 25.054±0.2°, 26.117±0.2°, 29.913±0.2°, 30.49±0.2°, 35.138±0.2°, 37.569±0.2°, and 37.972±0.2°; The infrared absorption peaks are shown in the following wave numbers:

3413 ($cm^{-1}$), 3353 ($cm^{-1}$), 3182 ($cm^{-1}$), 2961 ($cm^{-1}$), 2880 ($cm^{-1}$), 2797 ($cm^{-1}$), 1671 ($cm^{-1}$), 1491 ($cm^{-1}$), 1452 ($cm^{-1}$), 1398 ($cm^{-1}$), 1308 ($cm^{-1}$), 1240 ($cm^{-1}$), 1199 ($cm^{-1}$), 1081 ($cm^{-1}$), 1037 ($cm^{-1}$), 1012 ($cm^{-1}$), 947 ($cm^{-1}$), 671 ($cm^{-1}$), 613 ($cm^{-1}$), 462 ($cm^{-1}$).

Further, the infrared spectrum generated by crystalline form I of (R)-4-hydroxy-2-oxo-1-pyrrolidineacetamide of the present invention shows absorption peaks at the following wave numbers:

3413 ($cm^{-1}$), 3353 ($cm^{-1}$), 3182 ($cm^{-1}$), 2961 ($cm^{-1}$), 2880 ($cm^{-1}$), 2797 ($cm^{-1}$), 1671 ($cm^{-1}$), 1491 ($cm^{-1}$), 1452 ($cm^{-1}$), 1398 ($cm^{-1}$), 1308 ($cm^{-1}$), 1240 ($cm^{-1}$), 1199 ($cm^{-1}$), 1081 ($cm^{-1}$), 1037 ($cm^{-1}$), 1012 ($cm^{-1}$), 947 ($cm^{-1}$), 671 ($cm^{-1}$), 613 ($cm^{-1}$), 462 ($cm^{-1}$); the endothermic transition temperature is 133.1±2° C.

Further, the (R)-4-hydroxy-2-oxo-1-pyrrolidinylacetamide crystalline form I of the present invention has diffraction peaks at diffraction angles 2θ of 12.423±0.2°, 14.928±0.2°, 16.285±0.2°, and 16.465±0.2°, 17.344±0.2°, 19.198±0.2°, 20.459±0.2°, 20.707±0.2°, 21.548±0.2°, 21.889±0.2°, 23.203±0.2°, 25.054±0.2°, 26.117±0.2°, 29.913±0.2°, 30.49±0.2°, 35.138±0.2°, 37.569±0.2°, 37.972±0.2°; The unit cell is Orthorhombic (orthogonal crystal system), a=14.12 Å, b=5.82 Å, c=8.704 Å; the endothermic transition temperature is 133.1±2° C.; the infrared absorption peaks are shown in the following wave numbers:

3413 ($cm^{-1}$), 3353 ($cm^{-1}$), 3182 ($cm^{-1}$), 2961 ($cm^{-1}$), 2880 ($cm^{-1}$), 2797 ($cm^{-1}$), 1671 ($cm^{-1}$), 1491 ($cm^{-1}$), 1452 ($cm^{-1}$), 1398 ($cm^{-1}$), 1308 ($cm^{-1}$), 1240 ($cm^{-1}$), 1199 ($cm^{-1}$), 1081 ($cm^{-1}$), 1037 ($cm^{-1}$), 1012 ($cm^{-1}$), 947 ($cm^{-1}$), 671 ($cm^{-1}$), 613 ($cm^{-1}$), 462 ($cm^{-1}$).

According to a second aspect of the invention, the object of the present invention is to provide a process for the preparation of crystalline form I of (R)-4-hydroxy-2-oxo-1-pyrrolidineacetamide.

A method for preparing crystalline form I of (R)-4-hydroxy-2-oxo-1-pyrrolidineacetamide applies the following steps:

(1) Adding (R)-4-hydroxy-2-oxo-1-pyrrolidineacetamide to isopropanol or sec-butanol, stirring constantly, heating at from 30° C. to 100° C., filtering to form a supersaturated solution;

(2) Sealing and placing the supersaturated solution obtained in the step (1) in a low temperature environment of from −10° C. to −19° C. to cool and crystallize to obtain crystalline form I of (R)-4-hydroxy-2-oxo-1-pyrrolidineacetamide.

Further, the preparation method of the crystalline form I of (R)-4-hydroxy-2-oxo-1-pyrrolidineacetamide of the present invention applies the following steps:

(1) Adding (R)-4-hydroxy-2-oxo-1-pyrrolidinoacetamide in isopropanol or sec-butanol at 5 mg/mL to 50 mg/mL, stirring constantly, and heating at from 40° C. to 50° C., filtering to form a supersaturated solution;

(2) Sealing and placing the supersaturated solution obtained in the step (1) in a low temperature environment of from −15° C. to −19° C. to cool and crystallize to obtain crystalline form I of (R)-4-hydroxy-2-oxo-1-pyrrolidineacetamide.

According to a third aspect of the present invention, the present invention provides the use of crystalline form I of (R)-4-hydroxy-2-oxo-1-pyrrolidineacetamide for the preparation of anti-epileptic drugs. The use of the crystalline form I of (R)-4-hydroxy-2-oxo-1-pyrrolidineacetamide of the present invention for the preparation of anti-epileptic drugs preventing or treating acute seizures of epilepsy, in particular for the preparation of anti-epileptic drugs for preventing or treating acute and severe seizures of epilepsy. The use of crystalline form I of (R)-4-hydroxy-2-oxo-1-pyrrolidineacetamide of the present invention for the preparation of anti-epileptic drugs for preventing or treating generalized seizures. The use of crystalline form I of (R)-4-hydroxy-2-oxo-1-pyrrolidineacetamide of the present invention for the preparation of anti-epileptic drugs for preventing or treating partial seizure. The use of crystalline form I of (R)-4-hydroxy-2-oxo-1-pyrrolidineacetamide of the present invention for the preparation of anti-epileptic drugs for preventing or treating status epilepticus. The crystalline form I of (R)-4-hydroxy-2-oxo-1-pyrrolidineacetamide of the present invention exhibits special pharmacological activities in stabilization of abnormal cerebral discharge, sedation, anti-epilepsy, and the like; and it has solubility of more than or equal to 100 mg/mL in water, and a high bioavailability.

According to a fourth aspect of the present invention, the present invention provides a pharmaceutical composition comprising the crystalline form I of (R)-4-hydroxy-2-oxo-1-pyrrolidineacetamide described above, and a pharmaceutically acceptable excipient(s). The pharmaceutical composition of the present invention comprises a therapeutically effective amount of crystalline form I of (R)-4-hydroxy-2-oxo-1-pyrrolidineacetamide and a pharmaceutically acceptable excipient(s); the pharmaceutical composition can be administered to a patient by any acceptable route of administration, including, but not limited to, oral, rectal, vaginal, nasal, inhalation, topical (including transdermal) and parenteral administration, including tablets, powders, granules, injections, capsules, dripping pills, sustained release formulations, lyophilized powder injection.

Advantageous Effects

The present invention provides a crystalline form of (R)-4-hydroxy-2-oxo-1-pyrrolidineacetamide having diffraction peaks at 2θ of 12.423±0.2°, 16.465±0.2°, 17.344±0.2°, 21.889±0.2°, and 25.054±0.2°, wherein the relative peak intensity at the diffraction angle 2θ of 17.344±0.2° is 100%. The crystalline form of (R)-4-hydroxy-2-oxo-1-pyrrolidineacetamide of the present invention is capable of promoting the synthesis of phosphorylcholine and phosphoethanolamine, promoting cerebral metabolism, stimulating specific central nervous pathways through the blood-brain barrier, and has special biological activities in fields such as sedation, anti-epileptic and the like. The crystalline form I of (R)-4-hydroxy-2-oxo-1-pyrrolidineacetamide of the present invention has significant effects on the epileptic acute seizure, especially has significant inhibitory effects on the epileptic acute grand mal seizure; the crystalline form I of (R)-4-hydroxy-2-oxo-1-pyrrolidoneacetamide of the present invention has better inhibitory effects on all of epileptic generalized seizures, epileptic partial epileptic seizures and status epilepticus. Moreover, the crystalline form I of (R)-4-hydroxy-2-oxo-1-pyrrolidineacetamide of the present invention has high bioavailability and low toxicity and is suitable for development as an anti-epileptic drug. The crystalline form of (R)-4-hydroxy-2-oxo-1-pyrrolidone acetamide of the present invention has a melting point peak temperature of 133.1±2° C., fast dissolution rate in water, solubility of more than or equal to 100 mg/mL in water, and a high bioavailability. The crystalline form of (R)-4-hydroxy-2-oxo-1-pyrrolidineacetamide of the present invention is placed at a high temperature of 60° C. for 5 days, and the change of the related substance is tiny, and the stability to high temperature is great. Meanwhile, the particles of crystalline form of the (R)-4-hydroxy-2-oxo-1-pyrrolidinoacetamide of the present invention have good fluidity, can meet the liquidity requirement in the production process, which are suitable for the production of pharmaceutical preparations, storage and transportation; the crystalline form of (R)-4-hydroxy-2-oxo-1-pyrrolidinoacetamide of the present invention are suitable for making a variety of pharmaceutical compositions, and can be made into a variety of preparations such as tablets, capsules, dripping pills, sustained release formulations, lyophilized powder injections, etc. The preparation method of the invention adopts cheap and easily available raw material, and the prepared crystalline form of (R)-4-hydroxy-2-oxo-1-pyrrolidinylacetamide has high purity. The preparation method requires mild conditions and simple operations, introduces a low level of impurities and has a good reproducibility; the production process is easy to control, has a high safety and is suitable for industrial production.

DEFINITIONS

Figure 1:
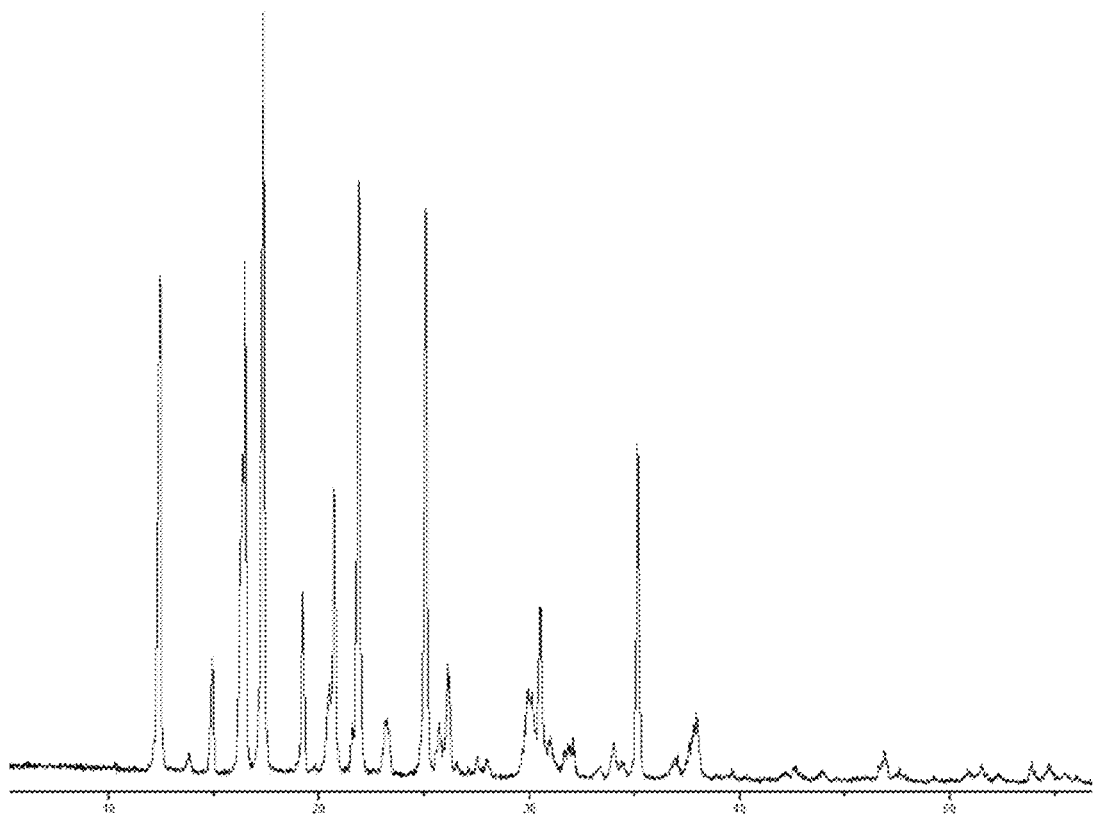
FIG. 1 is a powder diffraction pattern of the crystalline form I of (R)-4-hydroxy-2-oxo-1-pyrrolidineacetamide.

When describing the compounds, compositions and methods of the invention, the following terms have the following meanings, unless otherwise stated.

The term "therapeutically effective amount" means an amount that is sufficient to effect treatment when the amount is administered to a patient in need of treatment. As used herein, the term "treating" means treating a disease, illness or medical condition of a patient, for example, mammal (particularly human), comprising:

(a) preventing the occurrence of the disease, illness or medical condition, namely preventive treatment of the patient;

(b) improving the disease, illness or medical condition, namely eliminating or regressing the disease, illness or medical condition of the patient, including counteracting effects of other therapeutic agents;

(c) inhibiting a disease, illness or medical condition, namely mitigating or prohibiting the development of a disease, illness or medical condition of the patient; or (d) alleviating the symptoms of the disease, illness or medical condition of the patient.

It is noted that the singular form "a(n)" and "the", as in the description and the appended claims, can include plural referents, unless otherwise clearly stated in the content.

DETAILED DESCRIPTION OF THE PREFERRED EMBODIMENTS

The invention is described in detail by the following examples. It should be pointed out that the following examples are intended to further illustrate the invention and are not to be construed as limiting the scope of the invention. Some non-essential modifications and adjustments to the invention can be made by a person skilled in the art according to the aforementioned summary of the invention. All the raw materials and reagents of the present invention are commercially available products, wherein (R)-4-hydroxy-2-oxo-1-pyrrolidinoacetamide is provided by Chongqing Dongze Pharmaceutical Science and Technology Co., Ltd. The concepts of agitation, heating, filtration, and the like of the present invention are well known to a person skilled in the art and are carried out in accordance with conventional procedures in the art.

Preparation of Crystalline Form I of (R)-4-hydroxy-2-oxo-1-pyrrolidineacetamide

Example 1

50 mg of (R)-4-hydroxy-2-oxo-1-pyrrolidineacetamide was added to 2 mL of sec-butanol, stirred constantly, heated to 40° C., and filtered to obtain a supersaturated solution. The solution was sealed and placed in a −19° C. environment for 24 hours for cooling and crystallization, and a colorless sand crystal was obtained.

Example 2

The colorless sand crystal of (R)-4-hydroxy-2-oxo-1-pyrrolidinoacetamide obtained in Example 1 was subjected to crystalline parameter measurements, including powder diffraction measurement, infrared spectrum measurement, differential thermal scanning measurement, and thermogravimetric analysis. Test instrument conditions: the test uses DX 2500 X-ray diffractometer (Liaoning Dandong Fangyuan Instrument) to analyze the pre-oxidized and carbonized particles at various stages of the thermal stabilization process. Ni filter, CuKα was the radiation source, X-ray wavelength λ=0.1541 nm, acceleration voltage and current intensity were 40 kV and 50 mA respectively. Set the scanning interval to 0.02°, the scanning speed to 3°/min, and the scanning range to 5 to 45°. The crystalline prepared in Example 1 had diffraction peaks at diffraction angles 2θ of 12.423°, 14.928°, 16.285°, 16.465°, 17.344°, 19.198°, 20.459°, 20.707°, 21.548°, 21.889°, 23.203°, 25.054°, 26.117°, 29.913°, 30.49°, 35.138°, 37.569°, and 37.972°. The powder diffraction results were shown in FIG. 1, for convenience, the crystalline form was defined as crystalline form I of (R)-4-hydroxy-2-oxo-1-pyrrolidineacetamide.

The crystalline form I of (R)-4-hydroxy-2-oxo-1-pyrrolidineacetamide of the present invention had a powder X-ray pattern expressed by a crystalline plane spacing d, a Bragg angle (2θ), and a relative intensity percentage of crystalline form I, as shown below:

| 2-Theta | d(Å) | I % |
|---|---|---|
| 12.423 | 7.1193 | 73 |
| 14.928 | 5.9296 | 15.6 |
| 16.285 | 5.4386 | 46.2 |
| 16.465 | 5.3794 | 95.1 |
| 17.344 | 5.1086 | 100 |
| 19.198 | 4.6193 | 22.6 |
| 20.459 | 4.3374 | 28.4 |
| 20.707 | 4.286 | 43.5 |
| 21.548 | 4.1205 | 12.9 |
| 21.889 | 4.0572 | 83.1 |
| 23.203 | 3.8303 | 14.5 |
| 25.054 | 3.5513 | 73.1 |
| 26.117 | 3.4092 | 19.1 |
| 29.913 | 2.9846 | 36.7 |
| 30.49 | 2.9295 | 35.4 |
| 35.138 | 2.5519 | 44.8 |
| 37.569 | 2.3921 | 15 |
| 37.972 | 2.3677 | 18.4 |

Figure 2:
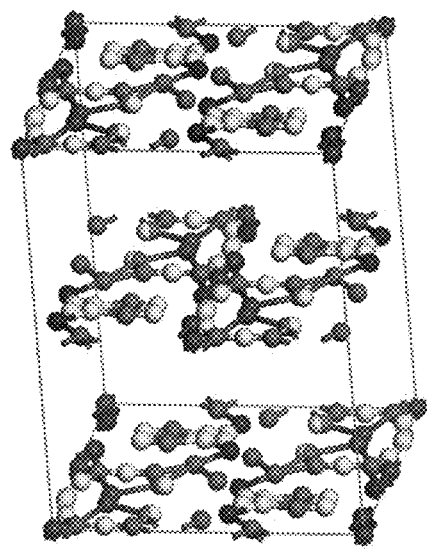
FIG. 2 is a crystalline structure diagram of the crystalline form I of (R)-4-hydroxy-2-oxo-1-pyrrolidineacetamide.

Crystalline Structure Pattern Determination:

The single crystalline structure of crystalline form I of (R)-4-hydroxy-2-oxo-1-pyrrolidineacetamide was analyzed, and its unit cell was Orthorhombic crystal system. The space group was a=14.122 Å, b=5.82 Å, c=8.704 Å; α=90.00°, β=90.00°, γ=90.00°, unit cell volume V=715.38 Å$^3$, and its crystalline structure was shown in FIG. 2:

The crystallographic parameters of crystalline form I of (R)-4-hydroxy-2-oxo-1-pyrrolidineacetamide of the present invention are shown in the following table:

| | Crystalline form I |
|---|---|
| Molecular formula | $C_6H_{10}N_2O_3$ |
| Molecular weight | 158.16 |
| Space group | $P4_1$ |
| test temperature/K | 150(2) |
| a, Å | 14.122 |
| b, Å | 5.82 |
| c, Å | 8.704 |
| α, deg | 90 |
| β, deg | 90 |
| γ, deg | 90 |
| V, Å$^3$ | 715.38 |

Differential Scanning Calorimetry (DSC) Pattern Determination:

Test instruments and conditions: DSC test was carried out using the NETZSCH DSC200PC type tester. The test method comprises: accurately weighing an amount (1-2 mg) of the sample in a DSC crucible, sealing the crucible with a lid, heating the crucible and an empty crucible as a reference from 20° C. to 200° C., placing an aluminum crucible in a nitrogen atmosphere, and heating at a rate of 3° C./min, where the nitrogen flow rate in the sample chamber is 20 mL/min. The differential scanning calorimetry (DSC) pattern of crystalline form I of (R)-4-hydroxy-2-oxo-1-pyrrolidineacetamide of the present invention was shown in FIG. 3, its endothermic transition temperature was around 133.1±2° C.

Infrared Spectrum (IR) Pattern Determination:

Test instruments and conditions: the NICOLET 6700 U.S.A Fourier transform infrared spectrometer was used, the measurement method was based on general rule of GB/T 6040-2002 infrared spectroscopy method, the sample was processed by solid potassium bromide pellet (24° C., 60%), and its infrared spectrum was determined. The infrared spectrum of crystalline form I of (R)-4-hydroxy-2-oxo-1-pyrrolidineacetamide was shown in FIG. 4, there are absorption peaks at wave numbers of 3413 (cm$^{-1}$), 3353 (cm$^{-1}$), 3182 (cm$^{-1}$), 2961 (cm$^{-1}$), 2880 (cm$^{-1}$), 2797 (cm$^{-1}$), 1671 (cm$^{-1}$), 1491 (cm$^{-1}$), 1452 (cm$^{-1}$), 1398 (cm$^{-1}$), 1308 (cm$^{-1}$), 1240 (cm$^{-1}$), 1199 (cm$^{-1}$), 1081 (cm$^{-1}$), 1037 (cm$^{-1}$), 1012 (cm$^{-1}$), 947 (cm$^{-1}$), 671 (cm$^{-1}$), 613 (cm$^{-1}$), 462 (cm$^{-1}$).

Figure 5:
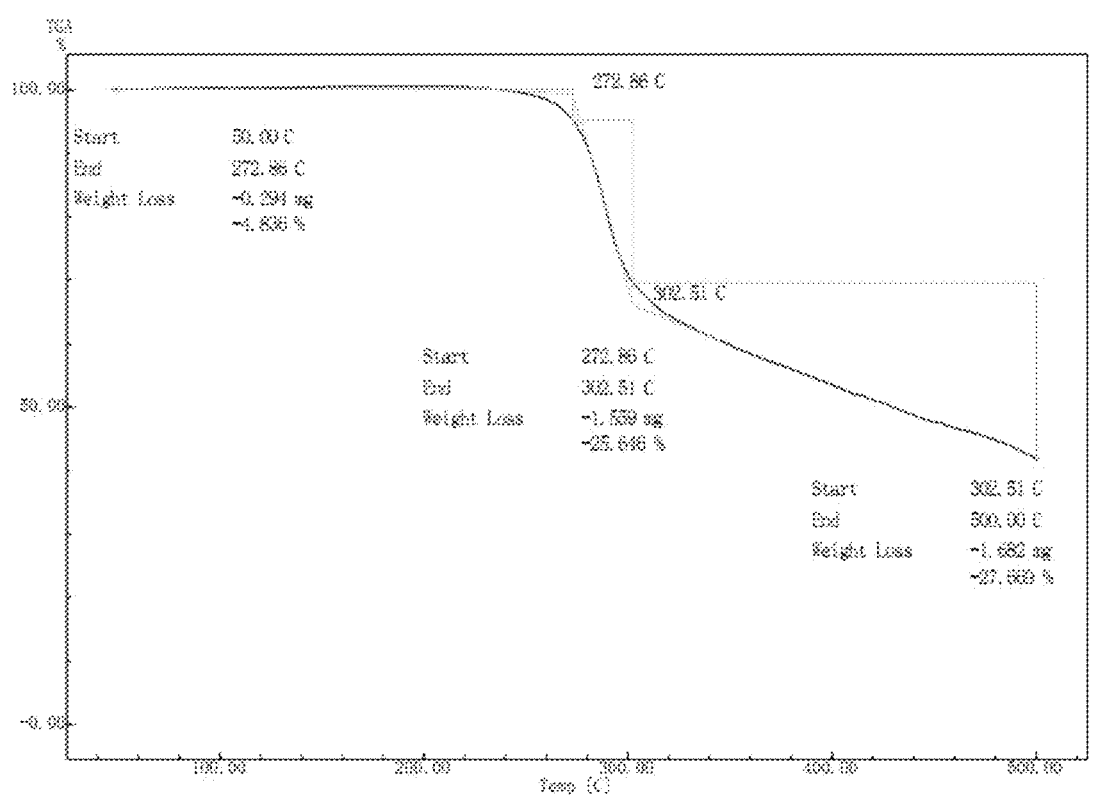
FIG. 5 is a thermogravimetric analysis (TG) pattern of crystalline form I of (R)-4-hydroxy-2-oxo-1-pyrrolidineacetamide.

Thermogravimetric Analysis (TG) Determination:

Test instruments and conditions: the test was carried out using Shimadzu DTG-60, the test method comprises: accurately weighing a certain amount (<5 mg) of the sample in aluminum crucible, the temperature rise rate was 10° C./min, the nitrogen flow rate was 50 mL/min, and the temperature was raised from room temperature (20° C.) to 600° C., α-Al$_2$O$_3$ was used as a reference, and the DTA-TGA curve was determined. The results of the thermogravimetric analysis (TG) of the crystalline form I of (R)-4-hydroxy-2-oxo-1-pyrrolidineacetamide of the present invention were shown in FIG. 5.

Example 3

20 mg of (R)-4-hydroxy-2-oxo-1-pyrrolidineacetamide was added in 2 mL of isopropanol, stirred constantly, heated to 50° C., filtered to obtain a supersaturated solution. The solution was sealed and placed in a −17° C. environment for 3 hours for cooling and crystallization, and a colorless sand crystal was obtained. It was identified by the method of Example 2 as the crystalline form I of (R)-4-hydroxy-2-oxo-1-pyrrolidineacetamide.

Example 4

1 g of (R)-4-hydroxy-2-oxo-1-pyrrolidineacetamide was added in 30 mL of sec-butanol, stirred constantly, heated to 45° C., and filtered to obtain a supersaturated solution. The solution was sealed and placed in a −18° C. environment for 36 hours for cooling and crystallization, and a colorless sand crystal was obtained. It was identified by the method of Example 2 as the crystalline form I of (R)-4-hydroxy-2-oxo-1-pyrrolidineacetamide.

Example 5

50 mg of (R)-4-hydroxy-2-oxo-1-pyrrolidineacetamide was added in 10 mL of isopropanol, stirred constantly, heated to 30° C., and filtered to obtain a supersaturated solution. The solution was sealed and placed in a −10° C. environment for 24 hours for cooling and crystallization, and a colorless sand crystal was obtained. It was identified by the method of Example 2 as the crystalline form I of (R)-4-hydroxy-2-oxo-1-pyrrolidineacetamide.

Example 6

60 mg of (R)-4-hydroxy-2-oxo-1-pyrrolidineacetamide was dissolved in 2 mL of sec-butanol solution, heated at 50° C. to dissolve, and filtered to obtain a supersaturated solution. The solution was sealed and placed in a −19° C. environment for 36 hours for cooling and crystallization, and a colorless sand crystal was obtained. It was identified by the method of Example 2 as the crystalline form I of (R)-4-hydroxy-2-oxo-1-pyrrolidineacetamide.

Example 7

100 mg of (R)-4-hydroxy-2-oxo-1-pyrrolidineacetamide was added to 2 mL of isopropanol, stirred constantly, heated at 100° C. and dissolved, filtered, and obtained a supersaturated solution. The solution was sealed and placed in an −18° C. environment for 36 hours for cooling and crystallization, and a colorless sand crystal was obtained. It was identified by the method of Example 2 as the crystalline form I of (R)-4-hydroxy-2-oxo-1-pyrrolidineacetamide.

Example 8

Stability test of the crystalline form I of (R)-4-hydroxy-2-oxo-1-pyrrolidineacetamideunder high temperature conditions. The crystalline form I of (R)-4-hydroxy-2-oxo-1-pyrrolidinylacetamide prepared in Examples 1 and 3-7 was placed in a flat weighing bottle and spread into thin layers of <5 mm thick, sealed in a clean container respectively and placed at 60° C. for 5 days; samples were taken and detected on day 0 and day 5, respectively. Each example was tested for 5 groups, and the average was obtained, the results are shown in the following table:
Changes at 60° C. High Temperature Conditions

|  | Day 0: Related substance | Day 5: Related substance | Related material changes |
|---|---|---|---|
| Example 1 | 0.23% | 0.35% | 0.12% |
| Example 3 | 0.22% | 0.36% | 0.14% |
| Example 4 | 0.26% | 0.39% | 0.13% |
| Example 5 | 0.25% | 0.37% | 0.12% |
| Example 6 | 0.26% | 0.37% | 0.11% |
| Example 7 | 0.22% | 0.33% | 0.11% |

As can be seen from the above table, the related substances of the crystalline form I of (R)-4-hydroxy-2-oxo-1-pyrrolidineacetamide of the present invention did not change much at a high temperature of 60° C., and the changes of the related substances in 5 days are less than 0.15%. Therefore, the crystalline form I of (R)-4-hydroxy-2-oxo-1-pyrrolidineacetamide of the present invention has good stability against high temperature.

Example 9

The angle of repose is the easiest way to check the fluidity of the powder, the smaller the angle of repose, indicates that the smaller the friction and the better the fluidity. In this test, the angle of repose of the crystalline form I of (R)-4-hydroxy-2-oxo-1-pyrrolidineacetamide prepared by the methods of Examples 1 and 3-7 was measured by an injection method (fixed funnel method). The samples to be tested were poured into the funnel, and they were gently and evenly dropped into the center of the disc to form a cone, when the materials fell freely from the oblique edge of the powder along the edge of the disc, the feedings were stopped, and the angles of repose were determined by the protractor; the sample traits and the clarity of the solution were examined, each example was tested for 5 groups and the average was obtained, the results are as follows:
Determination Results of the Samples Traits, Angle of Repose, Clarity of Solution, Etc

|  | sample trait | clarity of solution | angle of repose |
|---|---|---|---|
| Example 1 | white crystalline powder | clarification | 28.0 |
| Example 3 | white crystalline powder | clarification | 28.3 |
| Example 4 | white crystalline powder | clarification | 28.5 |
| Example 5 | white crystalline powder | clarification | 27.8 |
| Example 6 | white crystalline powder | clarification | 27.8 |
| Example 7 | white crystalline powder | clarification | 28.0 |

As can be seen from the test results in the above table, the particles of Examples 1, 3-7, that is, the crystalline form I of (R)-4-hydroxy-2-oxo-1-pyrrolidineacetamide of the present invention, have an angle of repose of less than 30 degrees, indicating good fluidity, which can meet the liquidity requirements in the production process, and is suitable for the production of pharmaceutical preparations, storage and transportation; therefore, the crystalline form I of (R)-4-hydroxy-2-oxo-1-pyrrolidinoacetamide of the present invention has better particle liquidity and better meets the production requirements as compared with the prior art.

(III) Preparation of Composition Comprises the Crystalline Form I of (R)-4-hydroxy-2-oxo-1-pyrrolidineacetamide

Example 10

1,000 capsules comprising crystalline form I of (R)-4-hydroxy-2-oxo-1-pyrrolidineacetamide were taken as examples, which were prepared by using 200 mg/capsule of the crystalline form I of (R)-4-hydroxy-2-oxo-1-pyrrolidineacetamide prepared by the method in Example 1, 80.8 mg/capsule lactose, 72 mg/capsule of carboxymethyl starch sodium, 7.2 mg/capsule of talcum powder and an appropriate amount of 10% polyvinylpyrrolidone. The specific preparation method was given as follows: the raw materials and excipients were firstly passed through an 80-mesh sieve; the above-mentioned amounts of the crystalline form I of (R)-4-hydroxy-2-oxo-1-pyrrolidineacetamide, lactose and carboxymethyl starch sodium were weighed and mixed uniformly, and 10% PVP ethanol solution was added to produce a soft material, pelletized, dried and granulated; the above-mentioned amount of talcum powder was added to the granules, mixed uniformly and filled into the capsules.

Example 11

1,000 tablets comprising crystalline form I of (R)-4-hydroxy-2-oxo-1-pyrrolidineacetamide were taken as examples, which were prepared by using 200 mg/tablet of the crystalline form I of (R)-4-hydroxy-2-oxo-1-pyrrolidineacetamide prepared by the method in Example 1, 34 mg/tablet of starch, 60 mg/tablet of microcrystalline cellulose, 6 mg/table of talcum powder and an appropriate amount of 2% hydroxypropyl methylcellulose (K4M). The specific preparation method was given as follows: the raw materials and excipients were firstly passed through an 80-mesh sieve; the above-mentioned amounts of crystalline form I of (R)-4-hydroxy-2-oxo-1-pyrrolidineacetamide, starch and microcrystalline cellulose were weighed and mixed uniformly, and an appropriate amount of 2% HPMC aqueous solution was added to produce a soft material, pelletized, dried and granulated; the prescription amount of talcum powder was added to the granules, mixed uniformly and pressed into the tablets.

Example 12

50 g of the crystalline form I of (R)-4-hydroxy-2-oxo-1-pyrrolidineacetamide prepared by the method in Example 1 and 150 g of glucose were dissolved in 500 ml of water for injection in a mixing equipment under controlling the temperature between 50° C. and 60° C., and stirred until completely dissolved. The solution was cooled to 25° C. The activated carbon was added into the above prepared solution for decolorization, and then the activated carbon was removed by filtration. Phosphate buffer was added to adjust pH of the solution to 4.0, followed by adding water for injection to 5000 ml, filling and sealing, and sterilizing at 105° C. for 30 min, and obtained an injection.

The invention claimed is:

1. A crystalline form I of (R)-4-hydroxy-2-oxo-1-pyrrolidineacetamide having diffraction peaks at diffraction angles 2θ of 12.423±0.2°, 16.465±0.2°, 17.344±0.2°, 21.889±0.2°, and 25.054±0.2°.

2. The crystalline form I of (R)-4-hydroxy-2-oxo-1-pyrrolidineacetamide according to claim 1, characterized in that the relative peak intensity at the diffraction angle 2θ of 17.344±0.2° is 100%; the relative peak intensity at the diffraction angle 2θ of 16.465±0.2° is greater than 90% and less than 100%; the relative peak intensities at the diffraction angles 2θ of 12.423±0.2°, 21.889±0.2°, and 25.054±0.2° are not less than 70%.

3. The crystalline form I of (R)-4-hydroxy-2-oxo-1-pyrrolidineacetamide according to claim 1 having diffraction peaks at diffraction angles 2θ of 12.423±0.2°, 16.285±0.2°, 16.465±0.2°, 17.344±0.2°, 20.707±0.2°, 21.889±0.2°, 25.054±0.2°, and 35.138±0.2°.

4. The crystalline form I of (R)-4-hydroxy-2-oxo-1-pyrrolidineacetamide according to claim 1 having diffraction peaks at diffraction angles 2θ of 12.423±0.2°, 14.928±0.2°, 16.285±0.2°, 16.465±0.2°, 17.344±0.2°, 19.198±0.2°, 20.459±0.2°, 20.707±0.2°, 21.548±0.2°, 21.889±0.2°, 23.203±0.2°, 25.054±0.2°, 26.117±0.2°, 29.913±0.2°, 30.49±0.2°, 35.138±0.2°, 37.569±0.2°, and 37.972±0.2°.

5. The crystalline form I of (R)-4-hydroxy-2-oxo-1-pyrrolidineacetamide according to claim 1 having a powder diffraction pattern as shown in FIG. 1.

6. The crystalline form I of (R)-4-hydroxy-2-oxo-1-pyrrolidineacetamide according to claim 1 having the following—X-ray powder diffraction data expressed by d(Å) value and relative intensity percentage I (%) value,

| d(Å) | I % |
|---|---|
| 7.1193 | 73 |
| 5.9296 | 15.6 |
| 5.4386 | 46.2 |
| 5.3794 | 95.1 |
| 5.1086 | 100 |
| 4.6193 | 22.6 |
| 4.3374 | 28.4 |
| 4.286 | 43.5 |
| 4.1205 | 12.9 |
| 4.0572 | 83.1 |

-continued

| d(Å) | I % |
|---|---|
| 3.8303 | 14.5 |
| 3.5513 | 73.1 |
| 3.4092 | 19.1 |
| 2.9846 | 36.7 |
| 2.9295 | 35.4 |
| 2.5519 | 44.8 |
| 2.3921 | 15 |
| 2.3677 | 18.4. |

7. The crystalline form I of (R)-4-hydroxy-2-oxo-1-pyrrolidineacetamide according to claim 1, characterized in that the unit cell of the crystalline form I of (R)-4-hydroxy-2-oxo-1-pyrrolidineacetamide is Orthorhombic (orthorhombic crystal system), a=14.122 Å, b=5.82 Å, and c=8.704 Å.

8. The crystalline form I of (R)-4-hydroxy-2-oxo-1-pyrrolidineacetamide according to claim 1, characterized by having a crystalline structure diagram as described in FIG. 2.

9. The crystalline form I of (R)-4-hydroxy-2-oxo-1-pyrrolidineacetamide according to claim 1, characterized in that the peak temperature of the melting point of the crystalline form I of (R)-4-hydroxy-2-oxo-1-pyrrolidineacetamide is 133.1±2° C.

Figure 3:
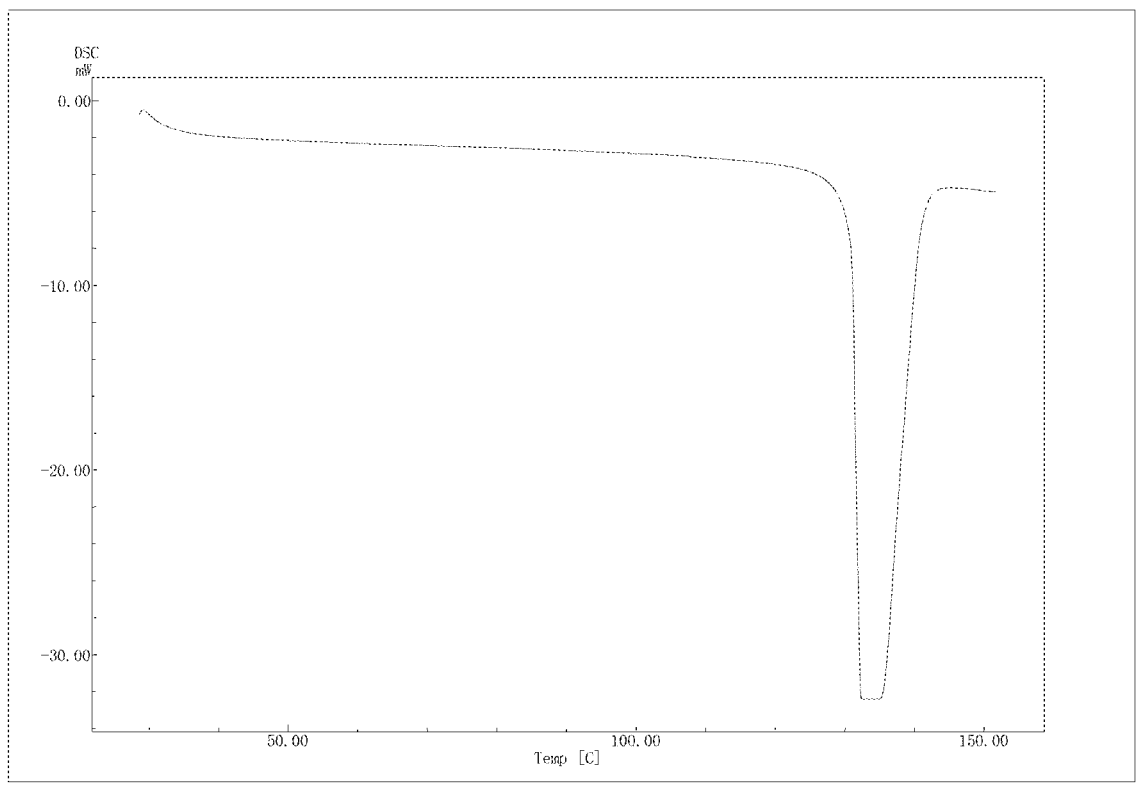
FIG. 3 is a differential scanning calorimetry (DSC) pattern of the crystalline form I of (R)-4-hydroxy-2-oxo-1-pyrrolidineacetamide.

10. The crystalline form I of (R)-4-hydroxy-2-oxo-1-pyrrolidineacetamide according to claim 1 characterized by having a differential scanning calorimetry (DSC) pattern as shown in FIG. 3.

11. The crystalline form I of (R)-4-hydroxy-2-oxo-1-pyrrolidineacetamide according to claim 1, characterized in that the infrared spectrum generated by the crystalline form I of (R)-4-hydroxy-2-oxo-1-pyrrolidineacetamide shows absorption peaks at the following wave numbers:
3413($cm^{-1}$), 3353($cm^{-1}$), 3182($cm^{-1}$), 2961($cm^{-1}$), 2880 ($cm^{-1}$), 2797($cm^{-1}$), 1671($cm^{-1}$), 1491($cm^{-1}$), 1452 ($cm^{-1}$), 1398($cm^{-1}$), 1308($cm^{-1}$), 1240($cm^{-1}$), 1199 ($cm^{-1}$), 1081($cm^{-1}$), 1037($cm^{-1}$), 1012($cm^{-1}$), 947 ($cm^{-1}$), 671($cm^{-1}$), 613($cm^{-1}$), 462($cm^{-1}$).

Figure 4:
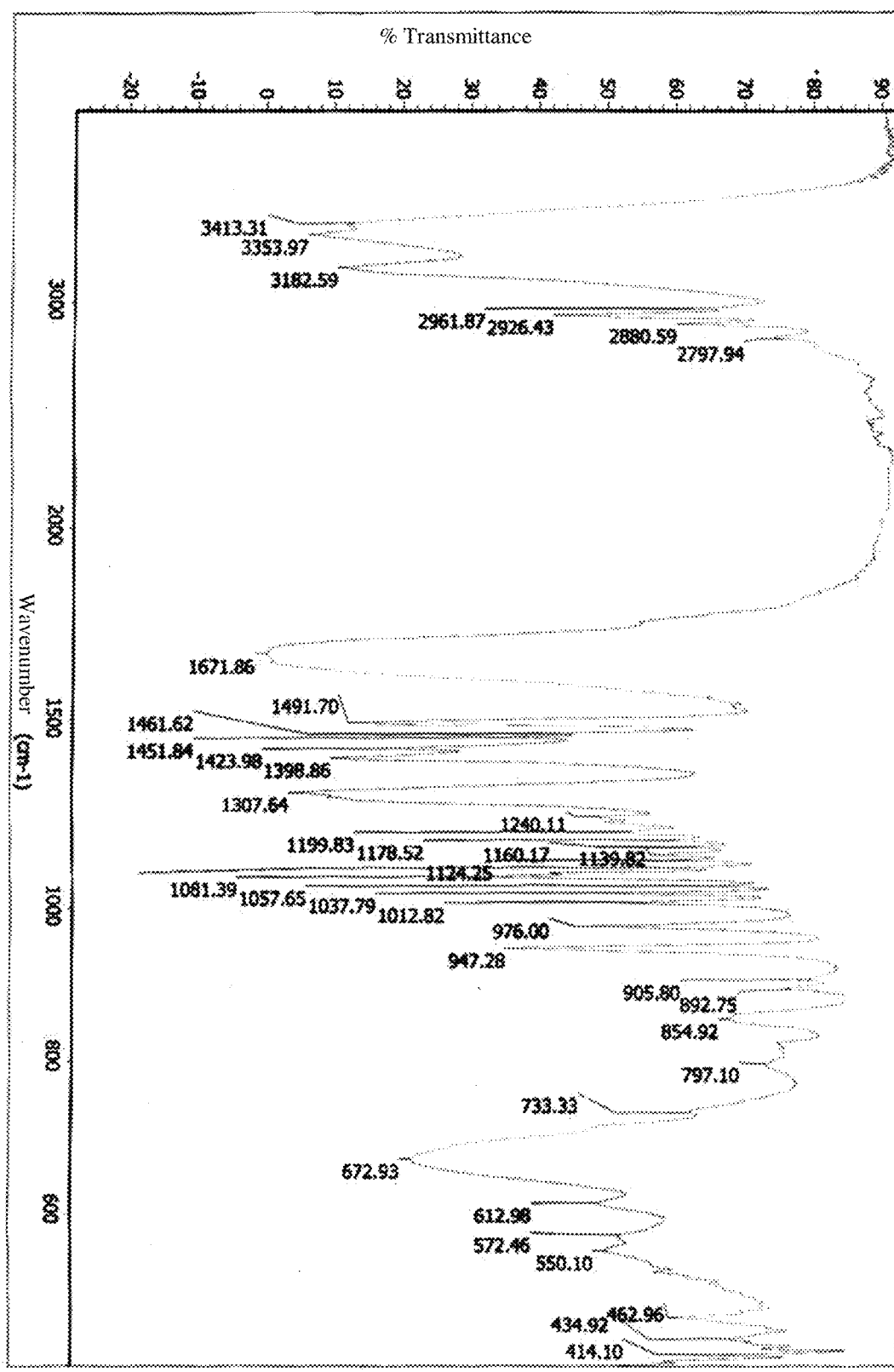
FIG. 4 is an infrared spectrum (IR) pattern of the crystalline form I (R)-4-hydroxy-2-oxo-1-pyrrolidineacetamide.

12. The crystalline form I of (R)-4-hydroxy-2-oxo-1-pyrrolidineacetamide according to claim 1 characterized by having an infrared spectrum as shown in FIG. 4.

13. A method for preparing a crystalline form I of (R)-4-hydroxy-2-oxo-1-pyrrolidineacetamide applying the following steps:
(1) Adding (R)-4-hydroxy-2-oxo-1-pyrrolidineacetamide to isopropanol or sec-butanol, stirring constantly, heating at from 30° C. to 100° C., filtering to form a supersaturated solution;
(2) Sealing and placing the supersaturated solution obtained in the step (1) in a low temperature environment of from −10° C. to −19° C. to cool and crystallize to obtain crystalline form I of (R)-4-hydroxy-2-oxo-1-pyrrolidineacetamide.

14. The method for preparing a crystalline form I of (R)-4-hydroxy-2-oxo-1-pyrrolidineacetamide according to claim 13 applying the following steps:
(1) Adding (R)-4-hydroxy-2-oxo-1-pyrrolidinoacetamide to isopropanol or sec-butanol at 5 mg/mL to 50 mg/mL, stirring constantly, and heating at from 40° C. to 50° C., filtering to form a supersaturated solution;
(2) Sealing and placing the supersaturated solution obtained in the step (1) in a low temperature environment of from −15° C. to −19° C. to cool and crystallize to obtain crystalline form I of (R)-4-hydroxy-2-oxo-1-pyrrolidineacetamide.

* * * * *